(12) United States Patent
Aikawa

(10) Patent No.: US 8,690,329 B2
(45) Date of Patent: Apr. 8, 2014

(54) FUNDUS CAPTURING APPARATUS

(75) Inventor: Satoshi Aikawa, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 233 days.

(21) Appl. No.: 13/205,873

(22) Filed: Aug. 9, 2011

(65) Prior Publication Data

US 2012/0050671 A1 Mar. 1, 2012

(30) Foreign Application Priority Data

Aug. 31, 2010 (JP) ................................. 2010-195068

(51) Int. Cl.
*A61B 3/14* (2006.01)
*A61B 3/15* (2006.01)

(52) U.S. Cl.
CPC ...................................... *A61B 3/152* (2013.01)
USPC .......................................... 351/208; 351/206

(58) Field of Classification Search
CPC ....................................................... A61B 3/152
USPC ......... 351/205, 206, 208, 210, 211, 214, 216, 351/221
See application file for complete search history.

(56) References Cited

U.S. PATENT DOCUMENTS

| 4,436,388 A | * | 3/1984 | Takahashi et al. ............. 351/206 |
| 2011/0007274 A1 | * | 1/2011 | Ono et al. ..................... 351/208 |
| 2012/0050670 A1 | | 3/2012 | Nakahara et al. |
| 2012/0050672 A1 | | 3/2012 | Aikawa |

FOREIGN PATENT DOCUMENTS

JP 2009-247772 A 10/2009

* cited by examiner

*Primary Examiner* — Huy K Mai
(74) *Attorney, Agent, or Firm* — Fitzpatrick, Cella, Harper & Scinto

(57) ABSTRACT

A fundus capturing apparatus, comprising: an irradiation unit adapted to irradiate light through an illumination light path onto a fundus of an eye to be examined; a capturing unit adapted to capture a fundus of the eye to be examined with reflection light of the light irradiated by the irradiation unit; a focus confirming unit adapted to confirm a focus state of the fundus captured by the capturing unit, the focus confirming unit being arranged on the illumination light path; a moving unit adapted to move the focus confirming unit on the illumination light path along a guide axis that is parallel to the illumination light path, in accordance with the focus state; and an advancing/retracting unit adapted to insert the focus confirming unit into the illumination light path or retract the focus confirming unit from the illumination light path by rotating it with respect to the guide axis.

8 Claims, 4 Drawing Sheets

FUNDUS CAPTURING APPARATUS

BACKGROUND OF THE INVENTION

1. Field of the Invention

The present invention relates to a fundus capturing apparatus.

2. Description of the Related Art

A split prism for observation in a fundus capturing apparatus (also referred to as "fundus camera" in the following) moves in an optical-axis direction in cooperation with the adjustment of a focus lens, and needs to perform an advancing and retracting movement, in which it enters the optical axis during observation and leaves the optical axis during capture. The configuration disclosed in Japanese Patent Laid-Open No. 2009-247772 is common, and this configuration example is explained with reference to FIG. 4.

A split prism driving mechanism 40 includes a split prism 401, a split base 402, a split shaft 403, a split advance/retract driving mechanism 404, a split advance/retract driving motor 405, a split shift base 406, a split shift shaft 407, a split shift anti-vibration shaft 408, and a split shift driving mechanism 409.

The split base 402, which holds the split prism 401, is fitted to the split shaft 403 such that it is rotatable with respect to the split shaft 403. When the split advance/retract driving motor 405 is operated, the split advance/retract driving mechanism 404 rotates the split base 402 with respect to the split shaft 403, and the split base 402 is retracted from the illumination optical axis. These components constituting a split advancing/retracting mechanism are fixed to the split shift base 406.

Moreover, when the split shift base 406 is driven by the split shift driving mechanism 409, the entire split advancing/retracting mechanism is moved along the split shift shaft 407 in the illumination optical-axis direction. It should be noted that at that time, it is moved in the illumination optical-axis direction while its rotation is limited by the split shift anti-vibration shaft 408.

It is uncertain where in the operation range the split shift operation stops, and it is necessary to perform an advancing/retracting operation from the location where it has stopped. Consequently, since the split advancing/retracting movement and the split shift movement need to be performed independently, a configuration is adopted, in which the entire split advancing/retracting mechanism is subjected to split shift movement.

However, in this conventional mechanism in which the entire split advancing/retracting mechanism is subjected to split-shifting, there is the problem that it is difficult to determine the split position with high precision.

The present invention provides a technique for determining the split position with high precision.

SUMMARY OF THE INVENTION

According to one aspect of the present invention, there is provided a fundus capturing apparatus, comprising: an irradiation unit adapted to irradiate light through an illumination light path onto a fundus of an eye to be examined; a capturing unit adapted to capture a fundus of the eye to be examined with reflection light of the light irradiated by the irradiation unit; a focus confirming unit adapted to confirm a focus state of the fundus captured by the capturing unit, the focus confirming unit being arranged on the illumination light path; a moving unit adapted to move the focus confirming unit on the illumination light path along a guide axis that is parallel to the illumination light path, in accordance with the focus state confirmed by the focus confirming unit; and an advancing/retracting unit adapted to insert the focus confirming unit into the illumination light path or retract the focus confirming unit from the illumination light path by rotating it with respect to the guide axis.

According to one aspect of the present invention, there is provided a fundus capturing apparatus, comprising: a focus marker projection unit adapted to project a focus marker via an illumination light path onto an eye to be examined; a moving unit adapted to move the focus marker projection unit along a movement axis that is parallel to the illumination light path, when putting the eye to be observed into focus; and a control unit adapted to retract the focus marker projection unit from the illumination light path by rotating the focus marker projection unit with the movement axis as the rotation axis, when capturing the eye to be examined.

Further features of the present invention will be apparent from the following description of exemplary embodiments with reference to the attached drawings.

DESCRIPTION OF THE EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
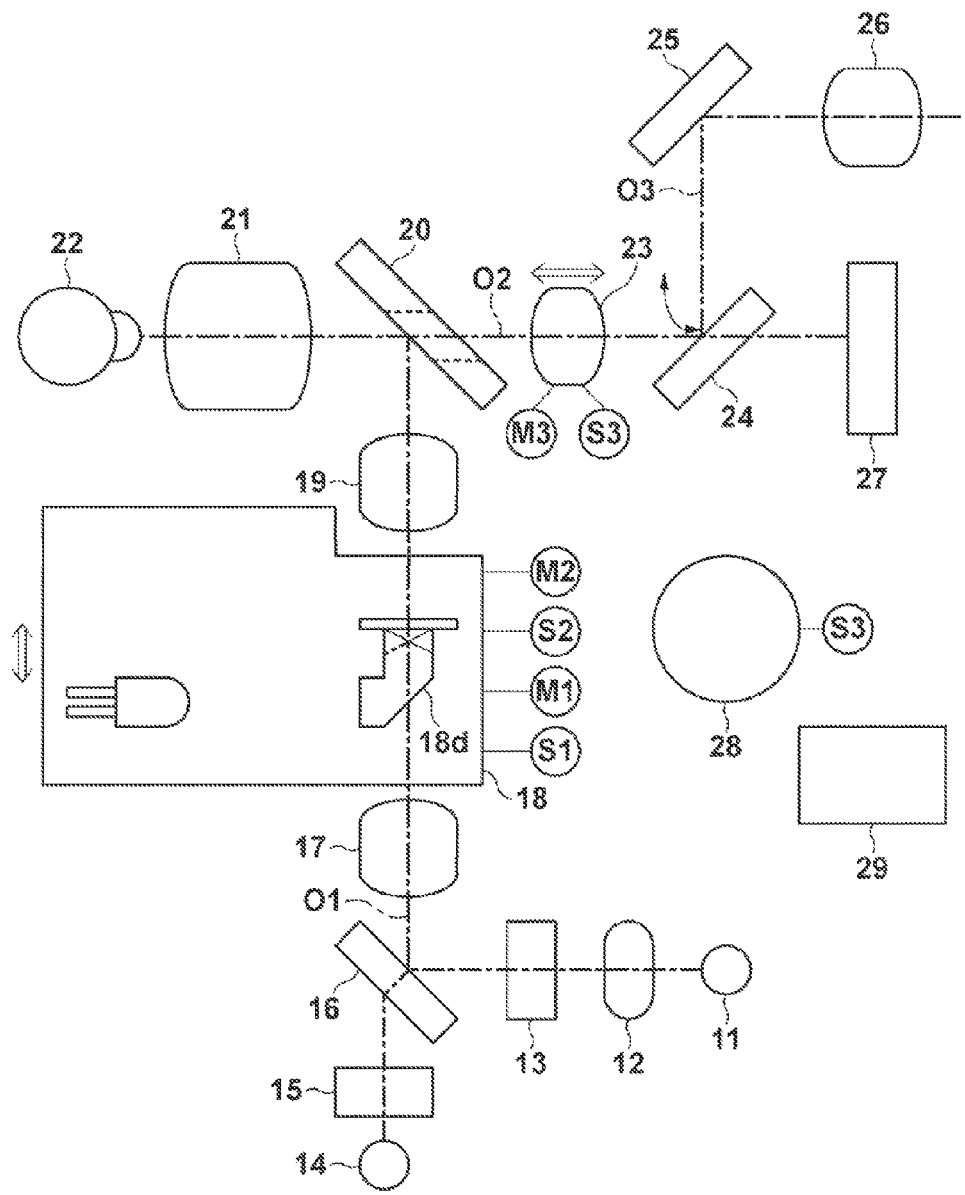
FIG. 1 is a schematic block diagram of a fundus capturing apparatus.

Referring to FIG. 1, a fundus capturing apparatus according to a first embodiment is explained. A halogen lamp 11 is a light source emitting visible light, which illuminates the fundus of a patient when observing the fundus with visible light. A xenon lamp 12 is a light source emitting visible light, which illuminates the fundus of a patient when capturing the fundus with visible light. A visible ring slit 13 is a mask for turning the illumination light from the halogen lamp 11 and the xenon lamp 12 serving as the visible light sources into ring-shaped illumination light. An infrared LED 14 serves as a light source when observing the fundus with infrared light. An infrared ring slit 15 is a mask for turning the illumination light from the infrared LED 14 into ring-shaped illumination light. An illumination mirror 16 is a dichroic mirror, which has the characteristics of reflecting visible light and passing infrared light. The light paths of the visible ring illumination light and the infrared ring illumination light are merged by this illumination mirror 16. Through an illumination light path 01, the ring illumination light is imaged by an illumination relay lens 17 and an illumination relay lens 19 onto an eye 22 to be examined.

A split unit 18 (also referred to as "focus marker projection unit") includes a light source (also referred to as "focus marker light source") for projecting a focus marker for confirming the focus state, and focus confirmation mechanism, such as a prism (also referred to as "splitting unit") for splitting light from a light source into a plurality of focus markers.

The split unit 18 is arranged on the illumination light path O1. The split unit 18 further includes a movement mechanism that moves the split unit 18 into the illumination light path O1 by advancing (inserting) the focus confirmation mechanism into the illumination light path O1 when observing the eye 22 to be examined and moving it in the arrow direction in the drawing, and an advancing/retracting mechanism (also referred to as "insertion mechanism for inserting/removing the focus marker projection unit into/from the light path") that retracts (removes) it from the illumination light path 01 when capturing the fundus of the eye 22 to be examined. A split shift driving motor M1 drives the split unit 18 in order to put the focus marker in focus, and a split shift position detecting unit S1 detects the stop position of the split unit 18. Moreover, a split advance/retract driving motor M2 advances/retracts the split unit 18 into/from the illumination light path O1. When observing the fundus, the split unit 18 is advanced into the illumination light path O1, and while observing, a focus marker is projected. On the other hand, when capturing, the split unit 18 is retracted from the illumination light path O1, and while capturing, a control is performed such that no focus marker is projected. A split advancing/retracting position detecting unit S2 detects a stop position of the split unit 18. An apertured mirror 20 is a total reflection mirror provided with an aperture in the center, which is configured such that the ring illumination light is reflected by an outer periphery of the mirror and capturing light passes through the aperture in the center. The ring illumination light that has passed the apertured mirror 20 is imaged by an objective lens 21 onto the eye 22 to be examined and illuminates the eye 22 to be examined. Reflected light thereof passes the objective lens 21 and is imaged onto the center of the apertured mirror 20. A capturing light path O2 is an optical axis reaching from the fundus image of the patient to a capturing element 27.

A focus lens 23 performs focus adjustment of the capturing light beam that has passed through the aperture in the center of the apertured mirror 20, by moving in the arrow direction in the drawing. A focus lens driving motor M3 adjusts the focus by driving the focus lens 23. A focus lens position detecting unit S3 detects a stop position of the focus lens 23. A movable mirror 24 is positioned as shown in the drawing when visually observing, guiding the capturing light to an observing light path O3, and is retracted by rotating it as indicated by the arrow in the drawing when observing with infrared light and when capturing, so that that the capturing light advances unhindered on the capturing light path O2. A fixed mirror 25 reflects the light on the observing light path O3 towards a finder eyepiece lens 26. With the finder eyepiece lens 26, an observer can observe the eye 22 to be examined. The capturing element 27 photoelectrically converts the capturing light and the obtained electrical signal is converted into digital data by a digital processing circuit not shown in the drawings. During infrared observance, the converted digital data is displayed on a display device not shown in the drawing, and during capturing, it is recorded on a recording medium not shown in the drawing.

By operating a focus adjustment knob 28, the observer can adjust the desired focus state. Using an observing light selection switch 29, the observer can select the observing light from visible light and infrared light.

Figure 2:
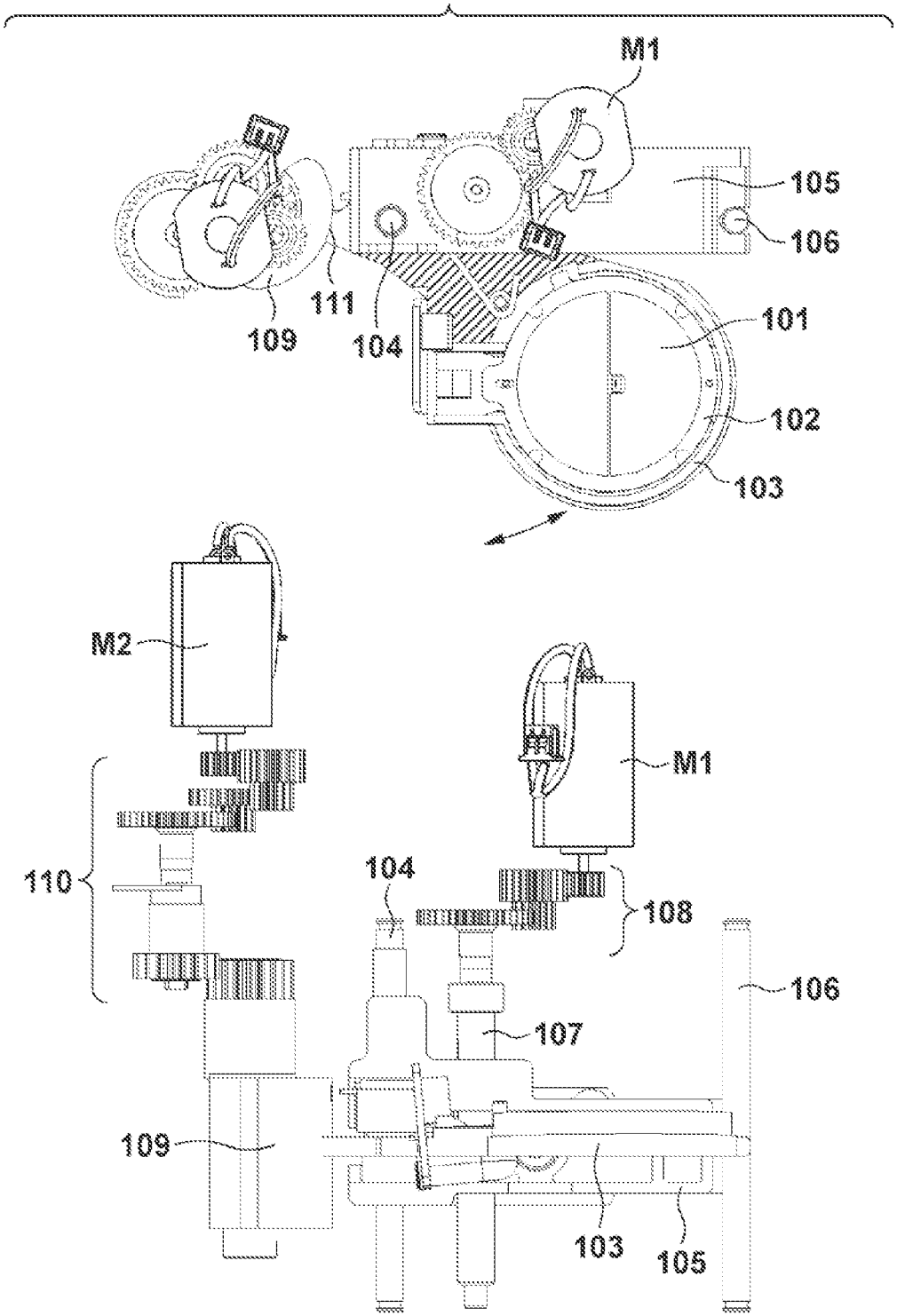
FIG. 2 is a diagram showing the structure of a split unit.

In the following, the structure of the split unit 18 is explained in detail, referring to FIG. 2. It should be noted that a base plate for holding the various components is omitted from FIG. 2. A split 101 is a transparent plate made of acryl, with a prism formed in the center. A split mask 102 is a mask for forming a prism image of the split 101. A split base 103 is a structural element that holds the split 101 to perform an advancing/retracting movement and a shifting movement. A split shaft 104, which is fitted to the shift base 103, serves as a guide axis (also referred to as "movement axis") for performing an advancing/retracting movement to rotate the split base 103 with the split shaft 104 as a reference axis, and for performing a shift movement that moves the split base 103 with the split shaft 104 as a translation axis. That is to say, the translation axis for the split shift movement and the rotation axis for the split advancing/retracting movement are the same. A split holder 105 is fitted to the split shaft 104 together with the split base 103, and holds the split base 103. A split anti-vibration shaft 106 prevents the rotation of split 101 during the shift movement, and supports the split 101 such that it moves parallel to the optical-axis direction on the illumination light path. The movement mechanism and the advancing/retracting mechanism of the split unit 18 may also be arranged at positions that are symmetrical with respect to the guide axis.

A split screw 107 is screwed to the split holder 105, and by rotating this split screw 107, the split holder 105 is moved in a direction parallel to the optical axis. A split shift driving source 108 gears down a driving torque of the split shift driving motor M1 and transmits it to the split screw 107. The split shift operation is carried out while monitoring the position in the shift direction of the split with the split shift position detecting unit S1 (not shown in the drawing).

The split base 103 is abutted (at a contact face 111) against a split advancing/retracting cam 109, and the split base 103 is advanced/retracted into/from the optical axis in accordance with the phase of the split advancing/retracting cam 109. This split advancing/retracting cam 109 does not follow the split shift operation. Consequently, the position where the split base 103 contacts the split advancing/retracting cam 109 (power transmission unit) changes with the split shift operation. The effective range of the split advancing/retracting cam 109 is set such that it encompasses the moving range of this split shift operation. That is to say, the effective range of the split advancing/retracting cam 109 needs to be at least the range over which the split shift operation can move. A split advance/retract driving source 110 gears down a driving torque of the split advance/retract driving motor M2 and transmits it to the split advancing/retracting cam 109. Moreover, the split advancing/retracting operation can be carried out while confirming its stop position with the split advancing/retracting position detecting unit S2 (not shown in the drawing).

Figure 3:
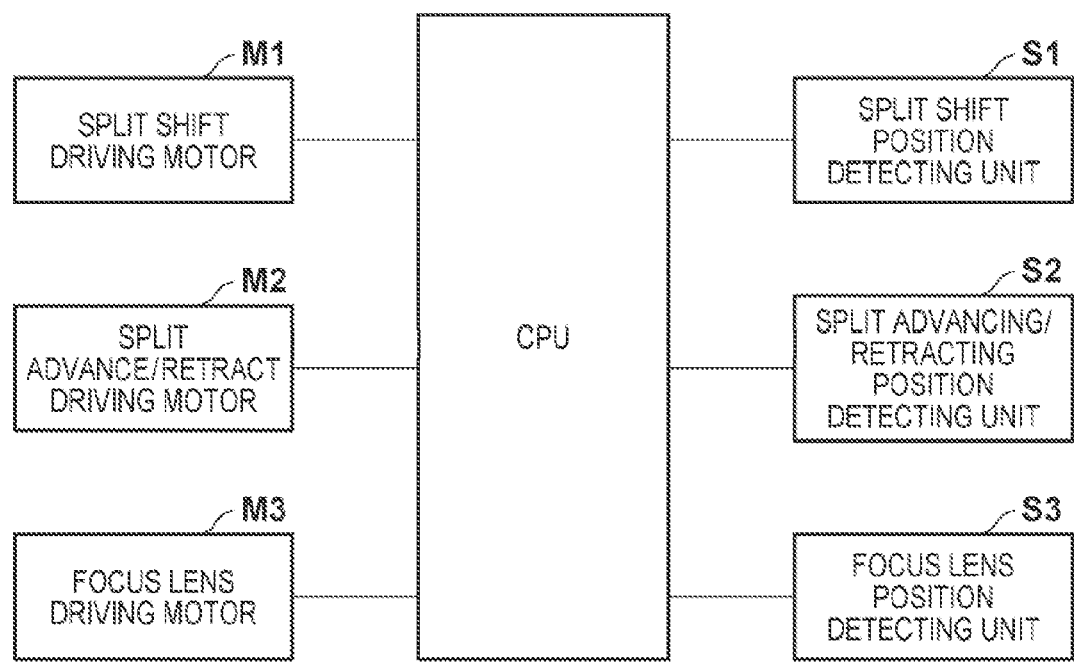
FIG. 3 is a functional block diagram showing how the split unit is driven.
Figure 4:
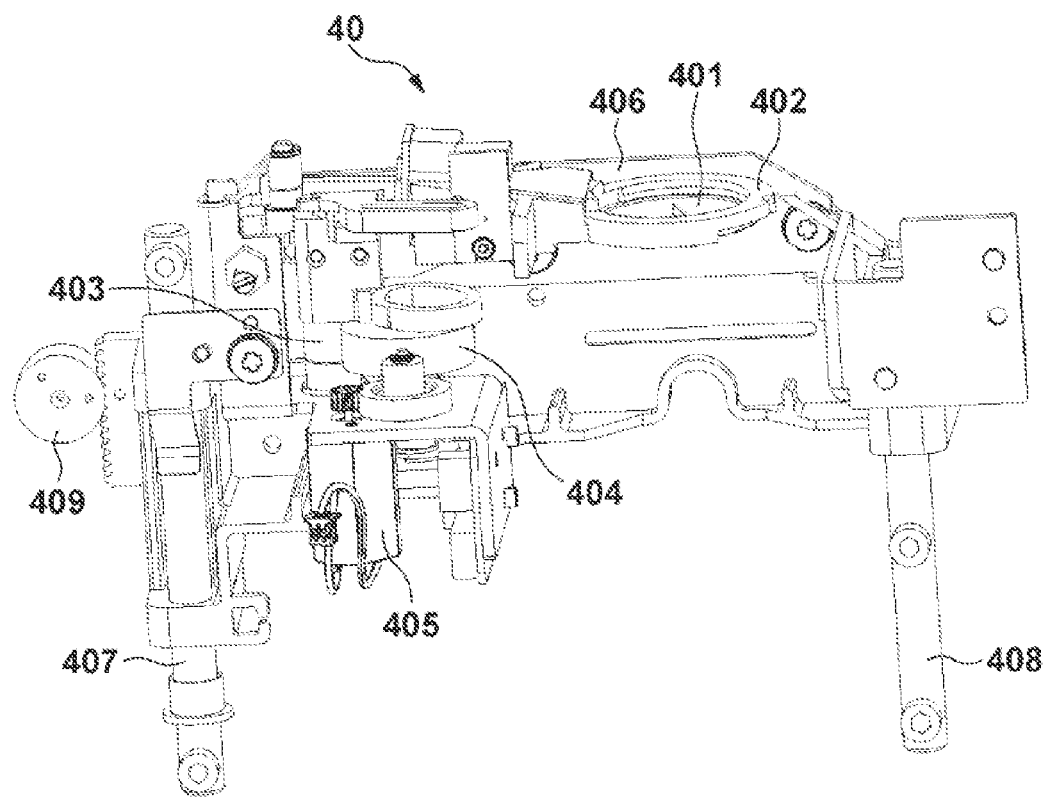
FIG. 4 is a diagram showing a conventional mechanism in which the entire split advancing/retracting mechanism is subjected to split shift movement.

Referring to FIG. 3, the following is an explanation of the functional configuration for driving the split unit 18. The overall control is carried out by a CPU, and the split shift driving motor M1 realizes feedback control using the split shift position detecting unit S1. Moreover, the split advance/retract driving motor M2 realizes feedback control using the split advancing/retracting position detecting unit S2. Moreover, the focus lens driving motor M3 realizes feedback control using the focus lens position detecting unit S3.

With the above-described configuration, the translation axis for shifting the split is the same as the rotation axis for advancing/retracting the split, so that it is not necessary to subject the entire split advancing/retracting mechanism to shift movement. Therefore, it is possible to determine the split position with high precision. Moreover, the overall split unit can be made more compact, and it is possible to realize a mechanism with simple configuration and high reliability.

With the present invention, it is possible to determine the split position with high precision.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-195068 filed on Aug. 31, 2010, which is hereby incorporated by reference herein in its entirety.

What is claimed is:

1. A fundus capturing apparatus, comprising:
   an irradiation unit adapted to irradiate light through an illumination light path onto a fundus of an eye to be examined;
   a capturing unit adapted to capture a fundus of the eye to be examined with reflection light of the light irradiated by the irradiation unit;
   a focus confirming unit adapted to confirm a focus state of the fundus captured by the capturing unit, the focus confirming unit being arranged on the illumination light path;
   a moving unit adapted to move the focus confirming unit on a guide shaft that is parallel to the illumination light path, for changing the focus state confirmed by the focus confirming unit; and
   an advancing/retracting unit adapted to insert the focus confirming unit into the illumination light path or retract the focus confirming unit from the illumination light path by rotating it on the guide shaft as a rotation axis.

2. The fundus capturing apparatus according to claim 1, wherein the moving unit and the advancing/retracting unit are arranged at positions that are symmetric with respect to the guide shaft.

3. The fundus capturing apparatus according to claim 1, wherein the advancing/retracting unit comprises a power transmission unit having a length that is at least a moving range that the focus confirming unit can be moved by the moving unit on the illumination light path.

4. The fundus capturing apparatus according to claim 1, wherein the focus confirming unit includes a splitting unit adapted to split light irradiated by a focus marker light source into a plurality of focus markers, and confirms the focus state of the fundus by projecting the plurality of focus markers, guided along the illumination light path, onto the fundus.

5. A fundus capturing apparatus, comprising:
   a focus marker projection unit adapted to project a focus marker via an illumination light path onto an eye to be examined;
   a moving unit adapted to move the focus marker projection unit along a movement shaft that is parallel to the illumination light path, when putting the eye to be observed into focus; and
   a control unit adapted to retract the focus marker projection unit from the illumination light path by rotating the focus marker projection unit on the movement shaft as the rotation axis, when capturing the eye to be examined.

6. The fundus capturing apparatus according to claim 5, further comprising:
   a capturing unit adapted to capture the eye to be examined and to obtain an image of the eye,
   wherein the capturing unit obtains the image after the focus marker projection unit is retracted from the illumination light path.

7. The fundus capturing apparatus according to claim 5, wherein the control unit comprises a power transmission unit having a length that is at least a moving range that the focus confirming unit can be moved by the moving unit on the illumination light path.

8. The fundus capturing apparatus according to claim 5, wherein the focus marker projection unit includes a splitting unit adapted to split light irradiated by a focus marker light source into a plurality of focus markers, and
   wherein the focus marker projection unit projects the plurality of focus markers, guided along the illumination light path, onto the eye to be examined.

* * * * *